US00RE36418E

United States Patent [19]

Almen et al.

[11] E Patent Number: Re. 36,418

[45] Reissued Date of Patent: Nov. 30, 1999

[54] CONTRAST MEDIA COMPRISING A NON-IONIC CONTRAST AGENT WITH LOW LEVELS OF SODIUM AND CALCIUM IONS

[75] Inventors: Torsten Almen; Lars Baath, both of Malmo, Sweden; Per Jynge, Trondheim; Audun Nesheim Oksendal, Oslo, both of Norway

[73] Assignee: Nycomed Imaging AS, Oslo, Norway

[21] Appl. No.: 08/616,245

[22] Filed: Mar. 15, 1996

Related U.S. Patent Documents

Reissue of:

[64] Patent No.: 5,328,680
Issued: Jul. 12, 1994
Appl. No.: 07/923,926
Filed: Nov. 6, 1992

[30] Foreign Application Priority Data

| | | | |
|---|---|---|---|
| Mar. 9, 1990 | [EP] | European Pat. Off. | 90 200580 |
| Sep. 14, 1990 | [GB] | United Kingdom | 90 20091 |

[51] Int. Cl.[6] ..... A61K 49/04

[52] U.S. Cl. ..... 424/9.45; 424/9.451; 424/9.454; 424/4.455; 424/900; 514/974

[58] Field of Search ..... 424/9.45, 9.451, 424/9.454, 9.455, 900; 514/974

[56] References Cited

U.S. PATENT DOCUMENTS

| | | | |
|---|---|---|---|
| 1,858,142 | 5/1932 | Elizey | 424/5 |
| 3,175,952 | 3/1965 | Bird | 424/5 |
| 3,325,370 | 6/1967 | Holtermann et al. | 424/5 |
| 3,347,746 | 10/1967 | Holtermann et al. | 424/5 |
| 4,283,381 | 8/1981 | Speck et al. | 424/5 |
| 4,364,921 | 12/1982 | Speck et al. | 424/5 |
| 4,426,371 | 1/1984 | Pfeiffer et al. | 424/5 |
| 4,649,050 | 3/1987 | Veech | 424/153 |
| 4,663,166 | 5/1987 | Veech | 424/146 |
| 4,963,344 | 10/1990 | Gries et al. | 424/9 |
| 5,011,925 | 4/1991 | Rajagopalan et al. | 544/58.1 |

FOREIGN PATENT DOCUMENTS

| | | |
|---|---|---|
| 11336/88 | 8/1988 | Australia . |
| 89/08101 | 9/1989 | WIPO . |
| 90/11094 | 10/1990 | WIPO . |

OTHER PUBLICATIONS

Piao et al. Investigative Radiology, 23:205–208, (1988).
Siman et al., AJR, 144:810–816 (1972).
Tragardh et al., Investigative Radiology, 10(3):231–238 (1975).
Morris, Investigative Radiology, 23(Suppl. 1):s137–s139, (Sep. 1988).
Kozeny et al., Am. Heart Journal 109:290 (1984).
Morris, *Investigative Radiology* 23:205–208 (Mar. 1988).
Zucker et al. *Investigative Radiology*, 23(Suppl. 2):s340–s345 (Nov. 1988).
Ralston et al., *Investigative Radiology*, 23(Suppl. 1):s140–s143 (Sep. 1988).
Almen, *Radiologica Diagnosis*, 17:439–448 (1976).
Bååth et al., *Acta Radiologica 30* (1988), 3 327–333.

*Primary Examiner*—Gary E. Hollinden
*Attorney, Agent, or Firm*—Bacon & Thomas, PLLC

[57] ABSTRACT

The physiological acceptability of contrast media, especially media for use in angiography, may be enhanced by inclusion of sub-plasma levels of sodium and calcium and, optionally, potassium and/or magnesium, for example 30 mM Na, 0.15 mM Ca, 0.9 mM K and 0.1 mM Mg.

12 Claims, No Drawings

CONTRAST MEDIA COMPRISING A NON-IONIC CONTRAST AGENT WITH LOW LEVELS OF SODIUM AND CALCIUM IONS

Matter enclosed in heavy brackets [ ] appears in the original patent but forms no part of this reissue specification; matter printed in italics indicates the additions made by reissue.

This invention relates to contrast media, especially to X-ray contrast media and more especially so-called non-ionic contrast media.

Contrast media generally fall into two groups, the so-called ionic and non-ionic contrast media. In these the contrast agent, in a carrier fluid, is respectively in ionic form or in molecular or particulate form.

Contrast media may be administered in medical imaging procedures, for example X-ray, magnetic resonance and ultrasound imaging, to enhance the image contrast in images of a subject, generally a human or non-human animal body. The resulting enhanced contrast enables different organs, tissue types or body compartments to be more clearly observed or identified. In X-ray imaging the contrast media function by modifying the X-ray absorption characteristics of the body sites into which they distribute; magnetic resonance contrast media generally function by modifying the characteristic relaxation times $T_1$ and $T_2$ of the nuclei, generally water protons, from the resonance signals of which the images are generated; and ultrasound contrast media function by modifying the speed of sound or the density in the body sites into which they distribute.

Clearly however the utility of a material as a contrast medium is governed to a large extent by its toxicity and any other adverse effects it may have on the subject to which it is administered. Since such media are conventionally used for diagnostic purposes rather than to achieve a direct therapeutic effect, when developing new contrast media there is a general desire to develop media having as little as possible an effect on the various biological mechanisms of the cells or the body as this will generally lead to lower animal toxicity and lower adverse clinical effects.

The toxicity and adverse effects of a contrast medium are contributed to by the components of the medium, e.g. the solvent or carrier as well as the contrast agent and its components (e.g. ions where it is ionic) and metabolites.

The following major contributing factors to contrast media toxicity and adverse effects have been identified:

the chemotoxicity of the contrast agent, the osmolality of the contrast medium, and the ionic composition (or lack thereof) of the contrast medium.

Thus in coronary angiography, for example, injection of contrast media into the circulatory system has been associated with several serious effects on cardiac function, effects sufficiently severe as to place limitations on the use in angiography of certain contrast media.

In this procedure, for a short period of time a bolus of contrast medium rather than blood flows through the circulatory system and differences in the chemical and physicochemical nature of the contrast medium and the blood that it temporarily replaces can give rise to undesirable effects, e.g. arrhythmias, QT-prolongation, and, especially, reduction in cardiac contractile force and occurrence of ventricular fibrillation. There have been many investigations into these negative effects on cardiac function of infusion of contrast media into the circulatory system, e.g. during angiography, and means for reducing or eliminating these effects have been widely sought.

By way of reassurance it should be noted that modern low osmolar non-ionic contrast media do not generally present significant toxic or adverse effects and are thus fully suitable for most patients. There is however a particular desire for even more physiologically balanced contrast media for use when there is a possibility of prolonged exposure of tissue to the contrast media, e.g. where pools of contrast media may form for example as a result of stenosis, wedging of a catheter, occlusion due to PTCA (percutaneous transluminal coronary angioplasty) intervention.

Most conventional X-ray contrast media contain as the contrast agent an iodine containing material. (Iodine which has a relatively high atomic weight accordingly has a relatively large cross-section to X-rays).

Thus the contrast medium used in angiography may have an iodine concentration as high as 250–450 mg I/ml and at that concentration range ionic contrast agents of ratio 1.5 (such as diatrizoate, iothalamate, ioxithalamate, iodamide and metrizoate) have an osmolality 5 to 9 times that of normal human plasma, ionic contrast agents of ratio 3 (e.g. ioxaglate) or non-ionic contrast agents of ratio 3 (e.g. metrizamide iopromide, iopentol, iopamidol and iohexol) have an osmolality about a half as large, and non-ionic contrast agents of ratio 6 (e.g. iotrolan and iodixanol) have an osmolality about quarter that of the ratio 1.5 ionic contrast agents at the same iodine concentration. Ratio 6 non-ionic contrast agents may even be used at iodine concentrations where they are hypotonic.

By "ratio 3" in the above paragraph it is meant that the ratio of iodine atoms to contrast agent particles (i.e. ions or molecules) is 3. Ratio 1.5 ionic and ratio 3 non-ionic contrast agents generally contain one triiodophenyl moiety and ratio 3 ionic and ratio 6 non-ionic contrast agents generally contain two triiodophenyl moieties.

Thus, for the most part, at iodine concentrations of for example 250 mg I/ml, X-ray contrast media will be hypertonic. This hypertonicity causes osmotic effects such as the draining out of water from red-blood cells, endothelial cells, and heart and blood vessel muscle cells. Loss of water makes red blood cells stiff and hypertonicity, chemotoxicity and non-optimal ionic makeup separately or together reduce the contractile force of the muscle cells and cause dilation of small blood vessels and a resultant decrease in blood pressure.

There is thus a general reluctance to add ions to isotonic or already hypertonic contrast media as this will result in or will increase hypertonicity and thus will increase osmotic side effects.

However, as mentioned above, an important contributory factor to the toxicity and adverse effects of contrast media is the ionic make-up of, or the total lack of ions in, the contrast medium. Of necessity, ionic contrast media contain counterions, generally countercations, to the iodinated ions which conventionally are anions. There has been a great deal of research into the cationic composition of these ionic contrast media and although commercially the cations are often sodium ($Na^+$) and/or meglumine ($Meg^+$), plasma ions such as calcium, potassium and magnesium may also be included.

While it has been generally accepted that cardiac muscle contractile force reduction is made more severe by increasing sodium ion concentration, the results of Almen (see Acta Radiologica Diagnosis 17: 439–448 (1976)) on a bat wing vein model for the determination of the effect of contrast media on smooth muscle contractility suggested that the absence of normal plasma ion concentrations of normal plasma cations (i.e. sodium, potassium, magnesium and calcium) adversely affects muscle contractivity. The results of Simon et al. AJR 114:801–816 (1972) for diatrizoate based ionic contrast media strongly suggested that there is a danger in coronary angiography of ventricular fibrillation where the sodium ion concentration in the contrast medium falls well beneath normal plasma levels. Further research has in general suggested that ventricular fibrillation occurs when sodium ion concentrations in contrast media fall below about 3.2 to 2.6 mM (see Morris in Investigative Radiology 23:S127–S129 (1988)). Indeed, there has also been concern that the incidence of ventricular fibrillation with non-ionic contrast media might be unacceptably high (see Piao et al. Investigative Radiology 23: 466–470 (1988)).

By adding calcium and magnesium ions to ionic contrast media containing sodium and meglumine cations, it has also been found that effects on the blood brain barrier can be decreased and that animal acute intravenous toxicity can also be reduced.

However our investigations have now shown that the addition of plasma levels of magnesium or calcium surprisingly can result in undesirable increases in the occurrence of arrhythmias, particularly ventricular fibrillation, and such levels of calcium can also result in an undesirable increase in cardiac contractile force.

Earlier research has also shown that the presence of sodium ions in contrast media results in reduced red blood cell aggregate formation in human blood and also in decreased erythrocyte aggregation. Zucker et al. (see Investigative Radiology 23: S340–S345 (1988)) have consequently suggested that the non-ionic X-ray contrast medium iohexol might be formulated to contain sodium, added as NaCl, at a concentration of 15 mM to decrease red blood cell aggregation without simultaneously causing an unacceptably large increase in osmolality.

However, while investigations have shown that the addition of plasma ions to X-ray contrast media may modify the biological effects of such media, it is recognised, as mentioned above, that any addition of ions to a hypertonic composition will increase hypertonicity and as a result will increase osmotic effects. Consequently while the literature shows that with contrast media the incidence of ventricular fibrillation and red blood cell aggregation may be reduced by incorporation within such media of low sodium concentrations and that undesirable changes in muscle cell contractile force may be decreased by inclusion of normal plasma concentrations of normal plasma cations, the literature does not show a consensus within the art and indeed is even contradictory regarding the optimal cation content for contrast media.

We have found however, as reported in WO-A-90/11094, that certain negative effects of nonionic contrast agents, in particular the incidence of arrhythmias (e.g. ventricular fibrillation), the aggregation of red blood cells and the reduction in cardiac contractile force, may be reduced or even eliminated by the inclusion of relatively low concentrations of sodium ions, e.g. about 30 mM, the improvement being such that this addition is justified even where the contrast medium is initially hypertonic.

We have now found that the undesired effects of contrast media in angiography may be reduced still further by inclusion of particular concentrations of salts of further plasma cations. In particular we have found that the negative effects of contrast media on cardiac contractile force and on red blood cell aggregation and the likelihood of the incidence of arrhythmias may be reduced still further.

Thus we have found in in vitro tests on human blood that the red blood cell aggregation inhibiting effect of adding electrolytes to X-ray contrast media is greater when more than one plasma cation is used. In animal models moreover we have found that inclusion of calcium produced further decrease in the adverse effects on cardiac contractile force beyond that achievable with sodium alone. More especially, by including calcium the initial cardiac contractile force reduction during coronary perfusion that can occur with sodium containing contrast media may be reduced or substantially eliminated. Calcium addition however has to be in relatively small quantities (generally the calcium to sodium ratio has to be below that in plasma) to avoid undesirable increases in the cardiac contractile force and to avoid increasing the occurrence of arrhythmias. In animal models we have also found that the incidence of arrhythmias (e.g. ventricular fibrillation) may be further reduced by the inclusion in such contrast media of relatively small quantities of potassium and/or magnesium. Furthermore we now find the inclusion of plasma cations in the contrast media, in particular non-ionic x-ray contrast media, serves to reduce the effect such media have of reducing the serum concentration of complement blood proteins. Moreover we find the effect of the added plasma alkaline earth metal cations of reducing red blood cell aggregation to be more pronounced than that of added plasma alkali metal cations.

[This] *Thus* viewed from one aspect the present invention provides a contrast medium comprising a physiologically tolerable aqueous carrier medium with dissolved therein a *non-ionic* contrast agent (preferably [a non-ionic contrast agent and also preferably an iodinated X-ray contrast agent, most preferably a non-ionic] *an* iodinated X-ray contrast agent)*;* [and a physiologically tolerable] *a* sodium [compound] *salt* providing a sodium ion concentration of 15 to 75 mM Na (preferably 20 to 70, especially preferably 25 to 35 mM Na[, characterized in that said carrier medium has dissolved therein at least one physiologically tolerable]*; a* calcium salt *providing a calcium ion concentration of 0.05 to 0.8 mM Ca (preferably 0.05 to 0.7, especially 0.1 to 0.6 and particularly 0.15 to 0.4 mM Ca), the ratio of concentrations of said sodium ion to said calcium ion provided by said sodium and calcium salts being greater than 55, preferably greater than 60, particularly 100 to 250;* and optionally also at least one salt selected from [physiologically tolerable] potassium and magnesium salts, the total concentration of said [calcium and] potassium [salts] *salt* being up to [0.8 mM Ca (preferably 0.05 to 0.7, especially 0.1 to 0.6 and particularly 0.15 to 0.4 mM Ca) and up to] 2 mM K (preferably 0.2 to 1.5, especially 0.3 to 1.2, particularly 0.4 to 0.9 mM K) [and in that the ratio of sodium to calcium ions is greater than 55, preferably greater than 60, particularly 100 to 250(the]. *The sodium calcium, potassium and magnesium salts are physiologically tolerable salts selected from the group consisting of chloride, phosphate and hydrogen carbonate salts. The* ratio of sodium to potassium ions *from said salts is* preferably also [being] greater than 15, more preferably greater than 20, more especially greater than 30, for example 25 to 80[)].

Preferably the osmolality of the contrast medium is at least 270, especially at least 280, more preferably at least 290 and especially preferably (particularly in the case where the contrast agent is a ratio 6 non-ionic X-ray contrast agent) 290–320 mosm/kg $H_2O$.

The contrast media of the invention preferably contain magnesium ions at a concentration of up to 0.8 mM Mg, preferably up to 0.6 mM Mg more especially up to 0.5 mM Mg, e.g. 0.05 to 0.4 mM Mg or more preferably 0.1 to 0.25 mM Mg. Where the media contain calcium and magnesium salts, the calcium to magnesium ratio will preferably be at least about 1.4, preferably at least about 1.5, possibly even at least that of normal plasma (about 2.9) or somewhat higher, e.g. 3 to 8.

The balance of the sodium to calcium ion ratio in the contrast media of the invention is particularly important in the cases of media containing lower ratio non-ionic X-ray contrast agents and of media with low sodium concentrations. Thus the sodium to calcium ratio is preferably greater than 300/n for "ratio n" contrast agents, especially greater than 350/n, more particularly greater than 375/n and most especially greater than 400/n.

Generally speaking the contrast media according to the invention will contain sodium and the other plasma cations in the following concentration ranges:

Sodium: 15–75 mM

Calcium: 0.05–0.6 mM

Potassium: 0.0–2.0 mM

Magnesium: 0.0–0.4 mM

While the contrast media according to the invention preferably contain a balanced mixture of all four plasma metal cations, sodium, calcium, potassium and magnesium, combinations of sodium and calcium and optionally one of potassium and magnesium may also be used, especially sodium and calcium, e.g. in the concentration ranges specified above. Calcium has been found to counteract the initial reduction in cardiac contractile force which occurs with sodium-containing contrast media and the combination of calcium with the other plasma cations not only enables this counteracting effect to be achieved at lower calcium concentrations than are necessary using calcium alone but also has a surprisingly beneficial effect of reducing the occurrence of arrhythmias.

In general, where the sodium concentration in the contrast medium is towards the upper end of the specified range the minimum desired sodium to alkaline earth metal cation ratios will be lower than at sodium concentrations towards the lower end of the specified range.

With contrast agents of ratio 6 or higher the maximum values for the ratios between the concentrations of the other plasma cations and sodium will be generally close (e.g. within 30%) to the ratios in normal plasma; with lower ratio contrast agents the maximum values for these plasma cation to sodium ratios will generally be lower, e.g. 50 or even 60% lower, than the plasma values (about 0.017, 0.026 and 0.006 for Ca, K and Mg).

For lower ratio contrast agents, the sodium ion concentration will preferably be in the range 25–35 mM Na and the other plasma cations will preferably be present in the following concentration ranges:

Calcium 0.1 to 0.3 mM, e.g. 0.1–0.2 mM

Potassium 0.0 to 1.2 mM, especially 0.3 to 0.9 mM, e.g. 0.3 to 0.6 mM

Magnesium 0.0 to 0.2 mM, especially 0.05 to 0.2 mM, e.g. 0.1 mM

Thus two particularly preferred compositions for lower ratio contrast agents contain the cations at (or within 0.05 mM of) the following concentrations:

Sodium: 30 mM

Calcium: 0.15 mM

Potassium: 0.90 mM or 0.40 mM

Magnesium: 0.10 mM

These concentrations and ranges of concentrations are generally preferred for lower ratio contrast agents at all normal iodine concentrations, e.g. 140–350 mgI/ml.

For the higher ratio contrast agents, compositions with base osmolalities below 290 mosm/kg $H_2O$ (i.e. compositions which are hypoosmotic in the absence of the salts) will preferably be brought to isotonicity or hypertonicity by the metal salts alone or by a combination of the metal salts and a physiologically tolerable, preferably non-ionic, osmoactive agent.

Non-ionic osmoactive agents, for example polyols, particularly saccharides or sugar alcohols especially hexitols, for example compounds such as mannitol, sorbitol, xylitol and glucose, may be used, generally in concentrations of up to 150 mM, preferably up to 100 mM, e.g. 30–80 mM (e.g. corresponding to osmolalities of up to 150 mosm/kg $H_2O$ etc.). Where such osmoactive agents are used, then the concentrations of sodium, potassium, calcium and magnesium specified above for the case of lower ratio contrast agents will preferably be used, e.g.:

Na: 25–35 mM, especially 30 mM

Ca: 0.1–0.3 mM, especially 0.1–0.2 mM

K: 0.0–1.2 mM, e.g. 0.3–0.6 mM

Mg: 0.0–0.2 mM, especially 0.05–0.2 mM

In this case, sufficient osmoactive agent (e.g. up to 80 mM) to make the contrast medium isotonic or slightly hypertonic (e.g. up to 320 mosm/kg $H_2O$) will be used. Two preferred examples of such a formulation use a ratio 6 contrast agent (at for example 150 mgI/ml) and contain the cations at (or within 0.05 mM of) the following concentrations Na: 30 mM Ca: 0.15 mM K: 0.9 mM and 0.4 mM Mg: 0.1 mM Mannitol: 80 mM Where the base osmolality of a higher ratio contrast agent composition is sufficiently close to isotonicity that only the metal salts need be used to bring the osmolality up to isotonicity (or slight hypertonicity), the concentrations used are preferably in the ranges:

Na: 65–75 mM

Ca: 0.3–0.6 mM

K: 0–2 mM, especially 0.5–2.0 mM

Mg: 0–0.4 mM, especially 0.1–0.4 mM

Preferred examples of such a formulation using a ratio 6 contrast agent (at for example 150 mgI/ml) contain the cations at (or within 0.05 mM of) the following concentrations:

Na: 70 mM

Ca: 0.40 to 0.6 mM, e.g. 0.4, 0.5 or 0.6 mM

K: 1.5 mM

Mg: 0.25 mM

Where a higher ratio contrast agent (e.g. iodixanol) is used at higher concentrations, e.g. 250 mgI/ml, especially 270–320 mgI/ml and particularly about 320 mgI/ml, metal salts are preferably added in amounts that are smaller but still sufficient to make the composition isoosmotic or only slightly hyperosmotic, e.g.

Na: 15–20 mM

Ca: 0.1–0.3 mM

X: 0.0–1.2 mM, e.g. 0.0 to 0.4 mM

Mg: 0.0–0.2 mM (for example Na 18.8 mM, Ca 0.3 mM, K 0 mM, Mg 0 mM or Na 18.8 mM, Ca 0.3 mM, K 0.6 mM, Mg 0.15 mM). Towards the lower end of the contrast agent concentration range (e.g., 250–300, especially 270, mgI/ml) the following cation concentration ranges will be more preferred:

Na: 25–35 mM
Ca: 0.1–0.5 mM
K: 0–1.2 mM, e.g. 0–0.6 mM
Mg: 0–0.2 mM
(for example Na 32.4 mM, Ca 0.5 mM, K 0 mM, Mg 0 mM).

In effect the present invention lies in the determination that negative effects of enhanced hyperosmolality resultant on providing a non-ionic X-ray contrast medium with a combination of metal cations are out-weighed by the resultant positive factors in terms of minimizing the occurrence of ventricular fibrillations and blood cell aggregation and the reduction in contractile force.

The present invention is especially applicable to X-ray contrast media containing contrast agents of ratio and 6, such as for example those mentioned below, especially iohexol, ioversol, iopamidol, iotrolan, ioxaglate and, particularly, iodixanol. (See GB-A-1548594, EP-A-83964, BE-A-836355, EP-A-33426, and EP-A-108638).

Other nonionic X-ray contrast agents which may be used according to the invention include: metrizamide (see DE-A-2031724), iodecimol (see EP-A-49745), ioglucol (see US-A-4314055), ioglucamide (see BE-A-846657), ioglunide (see DE-A-2456685), iogulamide (see DE-A-882309), iomeprol (see EP-A-26281), iopentol (see EP-A-105752), iopromide (see DE-A-2909439), iosarcol (see DE-A-3407473), iosimide (see DE-A-3001292), iotasul (see EP-A-22056), and ioxilan (see WO-A-87/00757).

The contrast media of the invention will particularly preferably contain such agents at concentrations of at least 100 mgI/ml. Moreover, while the general constraint that the deviation from isotonicity should if possible be minimized applies, it is generally preferable that the osmolality of the contrast media of the invention be less than 1 osm/kg $H_2O$, especially preferably 850 mosm/kg $H_2O$ or less.

[The sodium, calcium, potassium and magnesium ions may conveniently be incorporated within the contrast media of the invention in the form of salts with physiologically tolerable counterions. Particularly suitable counterions include plasma anions such as chloride, phosphate and hydrogen carbonate ions. However, the cations may alternatively be incorporated, at least in part, in the form of a salt of a physiologically tolerable chelating agent, e.g. sodium edetate or calcium disodium edetate.] The contrast media of the invention may conveniently be produced by the addition to existing contrast media of sodium, potassium, calcium and magnesium salts, either as solids or already in solution, or of salt mixtures or solutions thereof.

Viewed from a further aspect the invention thus also provides a process for the preparation of a contrast medium, said process comprising admixing, optionally after dispersion in a physiologically tolerable aqueous carrier medium, a contrast agent, a source of sodium ions, a physiologically tolerable calcium salt, if desired a further osmoactive agent, and if desired at least one physiologically tolerable potassium or magnesium salt, and if necessary diluting the resulting mixture whereby to produce a contrast medium according the invention.

The contrast media of the invention are particularly suited for intravascular administration and especially for use in cardiac imaging. Thus in a further aspect the present invention provides the use of a contrast agent, a physiologically tolerable sodium salt, physiologically tolerable calcium salt, if desired a further physiologically tolerable osmoactive agent and if desired at least one physiologically tolerable potassium or magnesium salt for the manufacture of a contrast medium according to the invention for use in cardiac imaging.

Preliminary investigations mentioned in WO-A-90/11094 indicated that for iodixanol or iohexol containing contrast media according to the claims of that application, the inclusion of 0.3 to 0.6 mM $Ca^{2+}$ or about 0.2 mM $Ca^{2+}$ respectively further enhanced the improvement in properties of the contrast media. Similarly, experimental results show oxygenation, e.g. oxygen saturation, of the media also to be effective in improving their properties.

While most particularly applicable to non-ionic contrast agents, the present invention is also applicable to ionic contrast agents, especially ionic iodinated X-ray contrast agents, e.g. ioxaglate (available from Guerbet SA under the trade name Hexabrix).

Thus viewed from a further aspect the invention also provides a contrast medium comprising a physiologically tolerable aqueous carrier medium with dissolved there an ionic contrast agent (e.g. ioxaglate), said contrast medium containing sodium and calcium and/or potasium ions and optionally also magnesium ions, the sodium ion concentration being up to 160 mM (especially 130 to 150 mM), the calcium concentration being up to 1.6 mM (especially up to 1.3, particularly about 1.2 mM) and the potassium concentration being up to 4.5 mM (especially about 4 mM). Such a contrast medium (e.g ioxaglate at about 330 mgI/ml, Na at about 140 mM, Ca at about 1.2 mM and K at about 4 mM) will preferably also contain magnesium ions, e.g. at up to 1 mM, especially about 0.8 mM.

The present invention will now be described further with reference the following non-limiting Examples.

EXAMPLE 1

Contrast Medium

Composition

Iohexol* (140 mg I/ml)
Sodium chloride to 30 mM $Na^+$
Calcium chloride to 0.15 mM $Ca^{2+}$
Potassium chloride to 0.4 mM $K^+$
Magnesium chloride to 0.10 mM $Mg^{2+}$

* Iohexol is available from Nycomed AS under the trade name OMNIPAQUE.

The solid chlorides are dissolved in iohexol to produce the-desired cation concentrations. Compositions containing the iohexol at 270, 300 and 350 mgI/ml and compositions containing potassium chloride to 0.9 mM $K^+$ are produced analogously. Any necessary dilution is effected with water for injections.

EXAMPLE 2

Contrast Medium

Composition

Iodixanol* (150 mgI/ml)
Sodium chloride to 30 mM $Na^+$
Calcium chloride to 0.15 mM $Ca^{2+}$
Potassium chloride to 0.4 mM $K^+$
Magnesium chloride to 0.10 mM $Mg^{2+}$
Mannitol to 80 mM The chlorides and mannitol are dissolved in iodixanol (available from Nycomed AS). Compositions containing the iodixanol at 180 mgI/ml and compositions containing potassium chloride to 0.9 mM $K^+$ are produced analogously. Any necessary dilution is effected with water for injections.

EXAMPLE 3

Contrast Medium

Composition

Iodixanol* (150 mgI/ml)
Sodium chloride to 70 mM $Na^+$
Calcium chloride to 0.4 mM $Ca^{2+}$
Potassium chloride to 1.5 mM $K^+$
Magnesium chloride to 0.25 mM $Mg^{2+}$ The chlorides are dissolved in iodixanol (available from Nycomed AS). A composition containing potassium chloride to 0.5 mM $K^{2+}$ is produced analogously. Any necessary dilution is effected with water for injections.

EXAMPLE 4

Contrast Medium

Composition

Iodixanol* (320 mgI/ml)
Sodium chloride to 30 mM $Na^+$
Calcium chloride to 0.15 mM $Ca^{2+}$
Potassium chloride to 0.40 mM $K^+$
Magnesium chloride to 0.10 mM $Mg^{2+}$ The chlorides are dissolved in iodixanol (available from Nycomed AS). Any necessary dilution is effected with water for injections. Compositions containing the iodixanol at 270 mgI/ml and compositions containing potassium chloride to 0.9 mM $K^+$ are produced analogously.

EXAMPLE 5

Contrast Medium

Composition

Iodixanol* (270 mgI/ml)
Sodium chloride to mM $Na^+$
Calcium chloride to 0.5 mM $Ca^{2+}$ The chlorides are dissolved in iodixanol (available from Nycomed AS). Any necessary dilution is effected with water for injections. A composition containing the iodixanol at 320 mgI/ml is produced analogously.

EXAMPLE 6

Contrast Medium

Composition

Iodixanol* (150 mgI/ml)
Sodium chloride to 70 mM $Na^+$
Calcium chloride to 0.6 mM $Ca^{2+}$ The chlorides are dissolved in iodixanol (available from Nycomed AS). Any necessary dilution is effected with water for injections.

EXAMPLE 7

Contrast Medium

Composition

Iodixanol* (320 mgI/ml)
Sodium chloride to 18.8 mM $Na^+$
Calcium chloride to 0.3 mM $Ca^{2+}$ The chlorides are dissolved in iodixanol (available from Nycomed AS). Any necessary dilution is effected with water for injections. A composition containing the sodium ions at 30 mM $Na^+$ is produced analogously.

EXAMPLE 8

Contrast Medium

Composition

Ioversol (300 mgI/ml)
Sodium chloride to 30 mM $Na^+$
Calcium chloride to 0.15 mM $Ca^{2+}$
Potassium chloride to 0.4 mM $K^+$
Magnesium chloride to 0.1 mM $Mg^{2+}$ The chlorides are dissolved in ioversol (available from Mallinckrodt, Inc.) and any necessary dilution is effected with water for injections. A composition containing potassium chloride to 0.9 mM $K^+$ is produced analogously.

Effects of Added Plasma Ions on the Change in Cardiac Contractile Force Caused by Bolus Injection of Contrast Media Calcium The changes in cardiac contractile force on injection of sodium ion containing contrast media without calcium, with sub-plasma levels of calcium and with plasma levels of calcium were demonstrated by determining the percentage change (relative to control period determined values) in left ventricular developed pressure (ALVDP) during (2–3 seconds) and at the end of exposure (4–5 seconds) to 0.5 ml of contrast media comprising iodixanol (150 mgI/ml), sodium (70 mM as NaCl) and 0, 0.2, 0.4, 0.6, 0.9 and 2.4 mM Ca (as $CaCl_2$) bolus injected to Langendorff perfused isolated rat hearts.

TABLE I

| Plasma ion concentration | | ΔLVDP(%)[a] | |
|---|---|---|---|
| Na(mM) | Ca(mM) | During exposure | At end of exposure |
| 70 | 0 | −49.4 ± 2.7 | −52.2 ± 4.3 |
| 70 | 0.2 | −31.3 ± 2.0 | −48.3 ± 5.0 |
| 70 | 0.4 | −24.6 ± 1.8 | −24.3 ± 2.3 |
| 70 | 0.6 | −16.2 ± 1.8 | −17.6 ± 2.9 |
| 70 | 0.9 | −6.8 ± 1.8 | +0.5 ± 1.7 |
| 70 | 2.4 | +31.2 ± 1.1 | +64.4 ± 4.7 |

[a]mean ± SEM, a = 6

The effect of 0, 0.1, 0.2, and 0.3 mM Ca (as $CaCl_2$) on contrast media comprising iohexol 140 mgI/ml and sodium 30 mM (as NaCl) were similarly determined, following 1 ml bolus injections.

TABLE II

| Plasma ion concentration | | ΔLVDP(%)[a] | |
|---|---|---|---|
| Na(mM) | Ca(mM) | During exposure | At end of exposure |
| 30 | 0.1 | −24.3 ± 3.8 | −29.8 ± 5.0 |
| 30 | 0.1 | −11.5 ± 2.2 | −3.9 ± 3.6 |

TABLE II-continued

| Plasma ion concentration | | ΔLVDP(%)[a] | |
|---|---|---|---|
| Na(mM) | Ca(mM) | During exposure | At end of exposure |
| 30 | 0.2 | −5.3 ± 2.2 | +7.4 ± 4.4 |
| 30 | 0.3 | +3.1 ± 2.5 | +17.7 ± 3.5 |

[a]mean ± SEM, a = 4

The effect of calcium for contrast media containing higher iodine concentrations were similarly demonstrated with 0.25 ml injections of contrast media containing iodixanol (300 mgI/ml), sodium (24 mM as NaCl) and 0, 0.2, and 0.4 mM Ca (as $CaCl_2$).

TABLE III

| Plasma ion concentration | | ΔLVDP(%)[a] | |
|---|---|---|---|
| Na(mM) | Ca(mM) | During exposure | At end of exposure |
| 24 | 0 | −25.9 ± 1.8 | −28.8 ± 3.4 |
| 24 | 0.2 | −24.7 ± 1.5 | −24.7 ± 2.6 |
| 24 | 0.4 | −14.3 ± 1.7 | −7.3 ± 1.1 |

[a]mean ± SEM, a = 6

The effect of calcium for contrast media in which osmolality is enhanced with an osmoactive agent (mannitol) rather than high sodium concentrations was similarly demonstrated for 1 ml injections of contrast media containing iodixanol (150 mgI/ml), sodium (30 mM as NaCl), mannitol (80 mosm/kg $H_2O$) and 0, 0.1, 0.2 and 0.3 mM Ca (as $CaCl_2$).

TABLE IV

| Plasma ion concentration | | ΔLVDP(%)[a] | |
|---|---|---|---|
| Na(mM) | Ca(mM) | During exposure | At end of exposure |
| 30 | 0 | −22.1 ± 0.7 | −39.6 ± 1.5 |
| 30 | 0.1 | −14.6 ± 1.2 | −16.3 ± 2.2 |
| 30 | 0.2 | −8.2 ± 0.3 | −4.7 ± 2.4 |
| 30 | 0.3 | −3.8 ± 2.0 | +6.8 ± 3.6 |

[a]mean ± SEM, a = 4

Further Plasma Cations

Using the same animal model, the effect of adding further plasma cations (from the chloride salts) to sodium containing contrast media was demonstrated with 1 ml injections of iohexol (140 and 350 mgI/ml) and iodixanol (150 and 320 mgI/ml).

TABLE V (Iohexol 140 mgI/ml)

| Plasma ion concentration | | | | ΔLVDP(%)[a] | |
|---|---|---|---|---|---|
| Na (mM) | Ca (mM) | K (mM) | Mg (mM) | During exposure | At end of exposure |
| 30 | 0 | 0 | 0 | −23.0 ± 3.1 | −28.4 ± 4.1 |
| 30 | 0.1 | 0.30 | 0.10 | −11.5 ± 2.6 | −10.0 ± 4.1 |

TABLE V-continued (Iohexol 140 mgI/ml)

| Plasma ion concentration | | | | ΔLVDP(%)[a] | |
|---|---|---|---|---|---|
| Na (mM) | Ca (mM) | K (mM) | Mg (mM) | During exposure | At end of exposure |
| 30 | 0.15 | 0.40 | 0.10 | −1.9 ± 0.7 | +7.3 ± 2.0 |
| 30 | 0.20 | 0.60 | 0.20 | −2.5 ± 2.4 | +6.0 ± 5.9 |
| 30 | 0.25 | 0.80 | 0.12 | +1.9 ± 2.7 | +20.4 ± 3.5 |

[a]mean ± SEM, a = 4

TABLE VI (Iohexol 350 mgI/ml)

| Plasma ion concentration | | | | ΔLVDP(%)*** | |
|---|---|---|---|---|---|
| Na (mM) | Ca (mM) | K (mM) | Mg (mM) | At end of exposure | Following exposure |
| 30 | 0 | 0 | 0* | −63.0 ± 0.6 | −84.0 ± 0.5 |
| 30 | 0.15 | 0.4 | 0.10** | −46.7 ± 1.1 | −62.8 ± 1.7 |

*a = 30
**a = 6
***mean ± SEM

TABLE VII (Iodixanol 150 mgI/ml)

| Plasma ion concentration | | | | ΔLVDP(%)** | |
|---|---|---|---|---|---|
| Na (mM) | Ca (mM) | K (mM) | Mg (mM) | During exposure | At end of exposure |
| 70 | 0 | 0 | 0 | −49.9 ± 2.5 | −74.9 ± 2.0 |
| 70 | 0.60 | 0 | 0 | −10.0 ± 1.9 | −15.1 ± 1.4 |
| 70 | 0.40 | 1.5 | 0.25 | −11.0 ± 0.8 | −21.2 ± 2.0 |
| 30* | 0.15 | 0.4 | 0.1 | −4.2 ± 1.1 | −2.2 ± 2.0 |

*plus 80 mosm/kg $H_2O$ mannitol
**mean ± SEM, a = 6

TABLE VIII (Iodixanol 320 mgI/ml)

| Plasma ion concentration | | | | ΔLVDP(%)[a] | |
|---|---|---|---|---|---|
| Na (mM) | Ca (mM) | K (mM) | Mg (mM) | At end of exposure | Following exposure |
| 18.8 | 0 | 0 | 0 | −31.6 ± 2.1 | −49.9 ± 2.8 |
| 18.8 | 0.3 | 0 | 0 | −21.7 ± 1.4 | −26.9 ± 2.5 |
| 30 | 0.15 | 0.4 | 0.1 | −33.8 ± 2.2 | −45.8 ± 2.2 |

[a]mean ± SEM, a = 4

Effect of Added Plasma Cations on Occurrence of Arrhythmias

Calcium

The effect of adding sodium (as NaCl) alone or sodium and sub-plasma levels of calcium to contrast media on the electrophysiological effects of bolus injections (about an order of magnitude greater than the volumes required for angiographic purposes) was measured on the isolated rabbit heart.

TABLE IX

| Contrast Agent (mgI/ml) | Na (mM) | Ca (mM) | % VF | % ES | % TD |
|---|---|---|---|---|---|
| Iohexol (350) | 30 | 0 | 0 | 0 | 0 |
| Iohexol (350) | 30 | 0.1 | 0 | 0 | 0 |
| Iohexol (350) | 30 | 0.2 | 0 | 0 | 0 |
| Iohexol (350) | 30 | 1.2 | 50 | 21 | 71 |
| Iodixanol (320) | 19 | 0 | 0 | 0 | 0 |
| Iodixanol (320) | 19 | 0.3 | 0 | 0 | 0 |

VF = Ventricular fibrillation
ES = Multiple extra symoli
TD = Total disturbances
Volume injected = 7.5 ml Other Plasma Cations The undesirability of adding plasma- or near plasma-levels of calcium and magnesium was demonstrated for iohexol (350 mgI/ml) (Tables IX above and Xl and XII below) and for iodixanol (320 mgI/ml) (Table X below). For the investigations reported in Tables XI and XII even larger volumes of contrast media were injected to ensure that the occurrence of arrhythmia was provoked so as to enable the cardioprotective effects of the different cations to be more easily visualized.

TABLE X

| Iodixanol (320 mgI/ml) | | | | | |
|---|---|---|---|---|---|
| Na (mM) | Ca (mM) | Mg (mM) | % VF | % ES | % TD |
| 28 | 0 | 0 | 0 | 0 | 0 |
| 28 | 2.5 | 0.95 | 67 | 33 | 100 |
| 19 | 1.2 | 0.6 | 30 | 0 | 30 |

Volume injected = 15 ml

TABLE XI

| Iohexol (350 mgI/ml) | | | | |
|---|---|---|---|---|
| Na (mM) | Ca (mM) | Mg (mM) | K (mM) | % VF |
| 30 | 0.15 | 0 | 0.4 | 20 |
| 30 | 0.15 | 1.2 | 0.4 | 90 |

Volume injected = 15 ml

TABLE XII

| Iohexol (350 mgI/ml) | | | | |
|---|---|---|---|---|
| Na (mM) | Ca (mM) | Mg (mM) | K (mM) | % VF |
| 30 | 0.15 | 0 | 0 | 40 |
| 30 | 0.15 | 0.1 | 0 | 30 |
| 30 | 0.15 | 0 | 0.4 | 20 |
| 30 | 0.15 | 0 | 0.9 | 10 |
| 30 | 0.15 | 0.1 | 0.4 | 15 |
| 30 | 0.15 | 0.1 | 0.9 | 10 |

Volume injected = 15 ml

Again using very large boli of contrast media the cardioprotective effect of adding calcium, magnesium and potassium cations to contrast media was demonstrated on 16 isolated rabbit hearts:

15 ml of iohexol (350 mgI/ml) caused ventricular fibrillation or asystolia in 14 of the 16 hearts (87.5%).

15 ml of iohexol (350 mgI/ml) with 30 mM NaCl caused ventricular fibrillation or asystolia in 4 of 16 hearts (25.0%).

15 ml of iohexol (350 mgI/ml) with 30 mM NaCl, 0.15 mM $CaCl_2$, 0.4 mM KCl and 0.1 mM Mg $Cl_2$ caused ventricular fibrillation or asystolia in 1 of 16 hearts (6%).

We claim:

1. A contrast medium composition comprising a physiologically tolerable aqueous carrier medium with dissolved therein: a non-ionic contrast agent; a [physiologically tolerable] sodium [compound] *salt* providing a sodium ion concentration of 15 to 75 mM Na; a [physiologically tolerable] calcium salt providing a calcium ion concentration of 0.05 to 0.8 mM Ca, *the ratio of concentrations of said sodium to said calcium ion provided by said sodium and calcium salts being greater than 60*; and optionally also at least one salt selected from [physiologically tolerable] potassium and magnesium salts, the total concentration of said *potassium salt being up to* 2 mM K; wherein [the ratio of sodium to calcium ions is greater than 55] *said salts are selected from the group consisting of chloride, phosphate or hydrogencarbonate salts*.

2. A composition as claimed in claim 1 containing [calcium] *said calcium salt* at a concentration of 0.05 to 0.7 mM $Ca^{2+}$.

3. A composition as claimed in claim 1 containing [calcium] *said calcium salt* at a concentration of 0.1 to 0.6 mM $Ca^{2+}$.

4. A composition as claimed in claim 1 containing [potassium] *said potassium salt* at a concentration of 0.2 to 1.5 mM $K^+$.

5. A composition as claimed in claim 1 [and] containing [potassium] *said potassium salt* at a concentration of 0.3 to 1.2 mM $K^+$.

6. A composition as claimed in claim 1 containing [magnesium] *said magnesium salt* at a concentration of up to 0.8 mM $Mg^{2+}$.

7. A composition as claimed in claim 1 containing [magnesium] *said magnesium salt* at a concentration of 0.5 to 0.4 mM $Mg^{2+}$.

8. A composition as claimed in claim 1 containing an iodinated X-ray contrast agent.

9. A composition as claimed in claim 8 containing a contrast agent selected from iohexol, ioversol, iopamidol, iotrolan, ioxaglate and iodixanol.

10. A composition as claimed in claim 8 wherein sodium, calcium, potassium and magnesium *salts* are present at concentrations of 25–35 mM $Na^+$, 0.1 to 0.3 mM $Ca^{2+}$, 0.3 to 1.2 mM $K^+$ and 0.05 to 0.2 mM $Mg^{2+}$ and wherein, where said contrast agent is of ratio 6 or greater, said medium contains a further physiologically tolerable osmoactive agent.

11. A composition as claimed in claim 8 wherein *said* sodium, calcium, potassium and magnesium *salts* are present at concentrations of 65–75 mM $Na^+$, 0.3–0.6 mM $Ca^{2+}$, 0.5–2.0 mM $K^+$ and 0.1–0.4 mM $Mg^{2+}$ and wherein said contrast agent is of ratio 6 or greater.

12. A composition as claimed in claim 1 having an osmolality of 290–320 mosm/kg $H_2O$.

* * * * *